United States Patent [19]

Holtkamp, Sr.

[11] Patent Number: Plant 6,430

[45] Date of Patent: Nov. 29, 1988

[54] AFRICAN VIOLET PLANT NAMED JULIANA

[76] Inventor: Reinhold Holtkamp, Sr., Werther Strasse 112, D4294 Isselburg, Fed. Rep. of Germany

[21] Appl. No.: 21,737

[22] Filed: Mar. 4, 1987

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of African violet named Juliana characterized by its single, bicolored, bright violet-blue and dark violet flowers; strong, upright flower stems that curve toward the center to form a bouquet above the leaves, profuse flowering, vigorous growth habit, flowering 9–10 weeks after potting, and its long-lasting and non-dropping flowers.

1 Drawing Sheet

The present invention comprises a new and distinct cultivar of African violet plant, botanically known as *Saintpaulia ionantha,* and hereinafter referred to by the cultivar name Juliana.

The new cultivar was referred to during the breeding and selection process by the designation H 29/4, and is a product of a planned breeding program. The new cultivar was originated from a cross made by me in the controlled breeding program in Isselburg, Federal Republic of Germany. The female, or seed parent, was a cultivar designated D 198/5 Blue Single. The male, or pollen parent, was a cultivar designated C 121/3 White Blue Single.

Juliana was discovered and selected by me in 1983 as a flowering plant within the progeny of the stated cross in a controlled environment in Isselburg, Federal Republic of Germany. Asexual reproduction of the new cultivar by leaf cuttings, as performed by me at Haffen, Federal Republic of Germany, has demonstrated that the combination of characteristics as herein disclosed for the new cultivar are firmly fixed and retained through successive generations of asexual reproduction.

Juliana has not been observed under all possible environmental conditions. The phenotype may vary significantly with variations in environment such as temperature, light intensity and day length. The following observations, measurements and values describe the new cultivar as grown in Haffen, Federal Republic of Germany and Nashville, Tenn., under greenhouse conditions which closely approximate those generally used in commercial practice.

The following traits have been repeatedly observed and are determined to be basic characteristics of Juliana which in combination distinguish this African violet as a new and distinct cultivar:

(1) Attractive, bicolored flowers, with the predominant color being a bright violet blue, and a relatively dark violet in and radiating from the center and on the edges.

(2) Strong, upright flower stems forming a tight bouquet above the leaves.

(3) In the first flash of flowers, the tight bouquet is formed.

(4) Profuse flowering.

(5) Each plant carries up to 8 and more upright flower stems; each carries 8–12 flowers.

(6) Vigorous grower.

(7) Plant saleable 9–10 weeks after potting.

(8) Medium green, shiny leaves, slightly hairy.

(9) Long-lasting, non-dropping, single flowers.

(10) After maturity the flowers dry off and remain on the peduncle without becoming infected with botrytis.

The accompanying color photographic drawing shows a typical specimen plant of the new cultivar. The colors appearing in the photograph are as true as possible with color illustrations of this type.

In the following description, color references are made to The Royal Horticultural Society Colour Chart (RHS), except where general colors of ordinary significance are referred to. Color values were taken under natural sunlight conditions at approximately 1:00 p.m. in Nashville, Tenn.

Botanical classification: *Saintpaulia ionantha,* Ramat., cv. Juliana.

Parentage:

*Male parent.*—C 121/3 White Blue Single.

*Female parent.*—D 198/5 Blue Single.

Propagation: The new cultivar holds its distinguishing characteristics through successive propagations by leaf cuttings.

Plant: From 6 cm to 8 cm tall when grown in pots, and approximately 22–25 cm in diameter when fully grown.

*Leaves.*—General form: Round to heart-shaped. Diameter: 65–75 mm. Texture: Leatherlike. Aspect: Shiny, slightly hairy. Veins: Underside is well pronounced, bright light green. Color (upper side): Green group 147A. Color (under side): Purple green between the veins, veins light green 148D. Petiole: Light green, hairy.

*Flowers.*—Buds: Bell-shaped, 6–7 mm before opening. Sepals: Five (5), spear-shaped. Calyx: Shape: Funnel-shaped. Aspect: Spear-shaped, hairy. Peduncle: Character: Strong, upright, hairy. Color: Greenish brown. Individual flowers: Size: 35–40 mm. Shape: Violet-shaped, single. Color (upper side): Predominantly 91D, with 88B in and radiating from center and on edges. Color (under side): 91C. Borne: Each stem carries 8–12 flowers on strong, upright peduncles. The stems stand above the leaves and form a compact flower head. Flowering habit: Flowering occurs 8–9 weeks after potting.

*Reproductive organs.*—Stamens: 2. Anthers: 2 with 4 anther cells, color 6B. Filaments: Purplish green. Pollen color: Yellow group 7a. Styles: 6 mm, dark purple.

*Roots.*—Normally developed, white turning slightly brownish when older.

Disease resistance: Good.

General observations: Juliana is a vigorous grower, with attractive medium green, slightly shiny leaves with indentations. Veins are well visible from the upperside. Approximately 9–10 weeks after potting the plant is saleable. In full flower, the plant develops 8–10 wirelike strong upright flower stems which carry 8 and more single bicolored flowers. These flowers are on strong peduncles which form a compact flower head that is freestanding above the leaves. The flowers are long-lasting and non-dropping.

I claim:

1. A new and distinct cultivar of African violet named Juliana, as described and illustrated, and particularly characterized by its single, bicolored, bright violet-blue and dark violet flowers; strong, upright flower stems that curve toward the center to form a bouquet above the leaves, profuse flowering, vigorous growth habit, flowering 9–10 weeks after potting, and its long-lasting and non-dropping flowers.

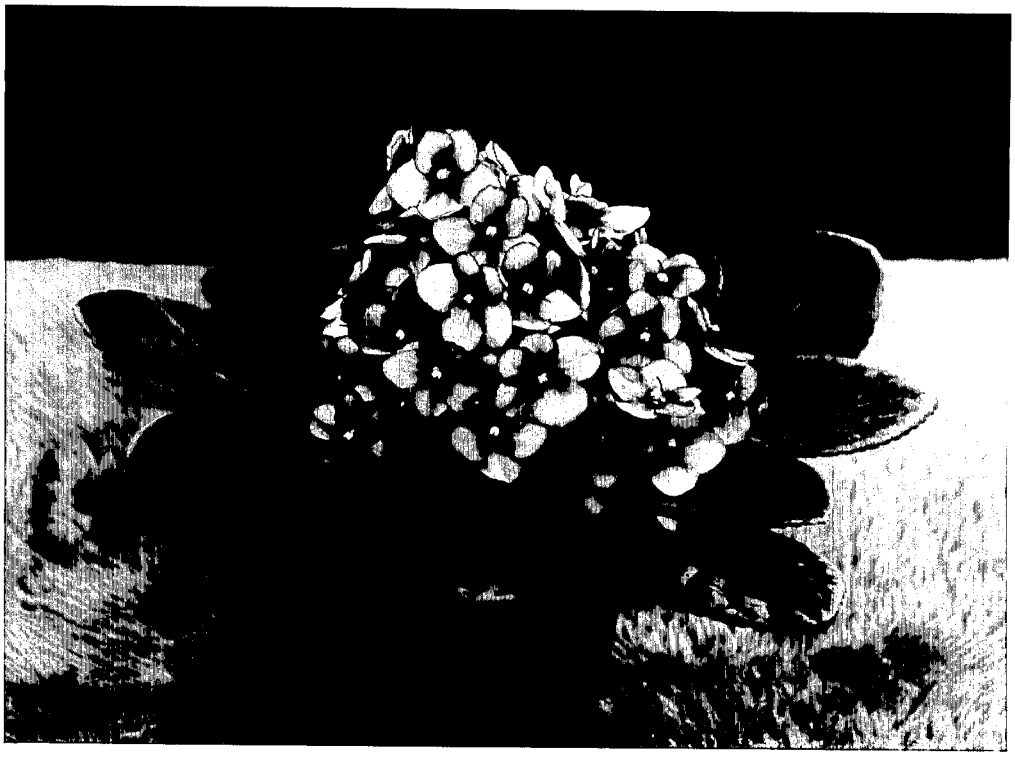

* * * * *